(12) United States Patent
Alexandersson

(10) Patent No.: US 11,160,933 B2
(45) Date of Patent: *Nov. 2, 2021

(54) MEDICAMENT DELIVERY DEVICE HAVING A CAP ASSEMBLY

(71) Applicant: SHL MEDICAL AG, Zug (CH)

(72) Inventor: Oscar Alexandersson, Haninge (SE)

(73) Assignee: SHL MEDICAL AG, Zug (CH)

( * ) Notice: Subject to any disclaimer, the term of this patent is extended or adjusted under 35 U.S.C. 154(b) by 348 days.

This patent is subject to a terminal disclaimer.

(21) Appl. No.: 16/344,623

(22) PCT Filed: Oct. 17, 2017

(86) PCT No.: PCT/EP2017/076495
§ 371 (c)(1),
(2) Date: Apr. 24, 2019

(87) PCT Pub. No.: WO2018/077672
PCT Pub. Date: May 3, 2018

(65) Prior Publication Data
US 2020/0061302 A1 Feb. 27, 2020

(30) Foreign Application Priority Data
Oct. 24, 2016 (EP) .................................... 16195281

(51) Int. Cl.
*A61M 5/32* (2006.01)
*A61M 5/315* (2006.01)
*A61M 5/50* (2006.01)

(52) U.S. Cl.
CPC ...... *A61M 5/3202* (2013.01); *A61M 5/31571* (2013.01); *A61M 5/5086* (2013.01)

(58) Field of Classification Search
CPC ............ A61M 5/3202; A61M 5/31571; A61M 5/31535; A61M 5/5086;
(Continued)

(56) References Cited

U.S. PATENT DOCUMENTS

2015/0174325 A1* 6/2015 Young ................. A61M 5/2033
604/135
2016/0325044 A1 11/2016 Tschirren et al.

FOREIGN PATENT DOCUMENTS

CN 1419458 A 5/2003
CN 101563125 A 10/2009
(Continued)

OTHER PUBLICATIONS

Chinese Office Action for CN Application No. 201780059289.6, dated Nov. 30, 2020.

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP

(57) ABSTRACT

The present disclosure relates to a medicament delivery device comprising: a housing having a proximal and distal end; a medicament container positioned in the housing and having a medicament delivery member shield; a medicament delivery mechanism associated with the medicament container; an activation member operably connected to the medicament delivery mechanism and longitudinally movable in relation to the housing from an extended position to a retracted position to activate the medicament delivery mechanism; and a removable cap assembly comprising an outer tubular cap body and an inner tubular integrity lock member coaxially coupled to the outer tubular cap body; wherein in a first position of the removable cap assembly, a resilient structure of the inner tubular integrity lock member is engaged to a first engaging structure of the activation member and a second engaging structure of the housing for preventing the activation member from moving into the retracted position.

15 Claims, 12 Drawing Sheets

(58) Field of Classification Search
CPC .. A61M 2005/2073; A61M 2005/3117; A61M 5/20; A61M 5/315
See application file for complete search history.

(56) References Cited

FOREIGN PATENT DOCUMENTS

| | | |
|---|---|---|
| CN | 103442756 A | 12/2013 |
| CN | 103492002 A | 1/2014 |
| EP | 2745866 A1 | 6/2014 |
| GB | 2511317 A | 9/2014 |
| WO | 2012085579 A2 | 6/2012 |
| WO | 2012096620 A1 | 7/2012 |
| WO | 2013048310 A1 | 4/2013 |
| WO | 2013119591 A1 | 8/2013 |
| WO | 2014131858 A1 | 9/2014 |
| WO | 2015011488 A1 | 1/2015 |
| WO | 2016051168 A2 | 4/2016 |

* cited by examiner

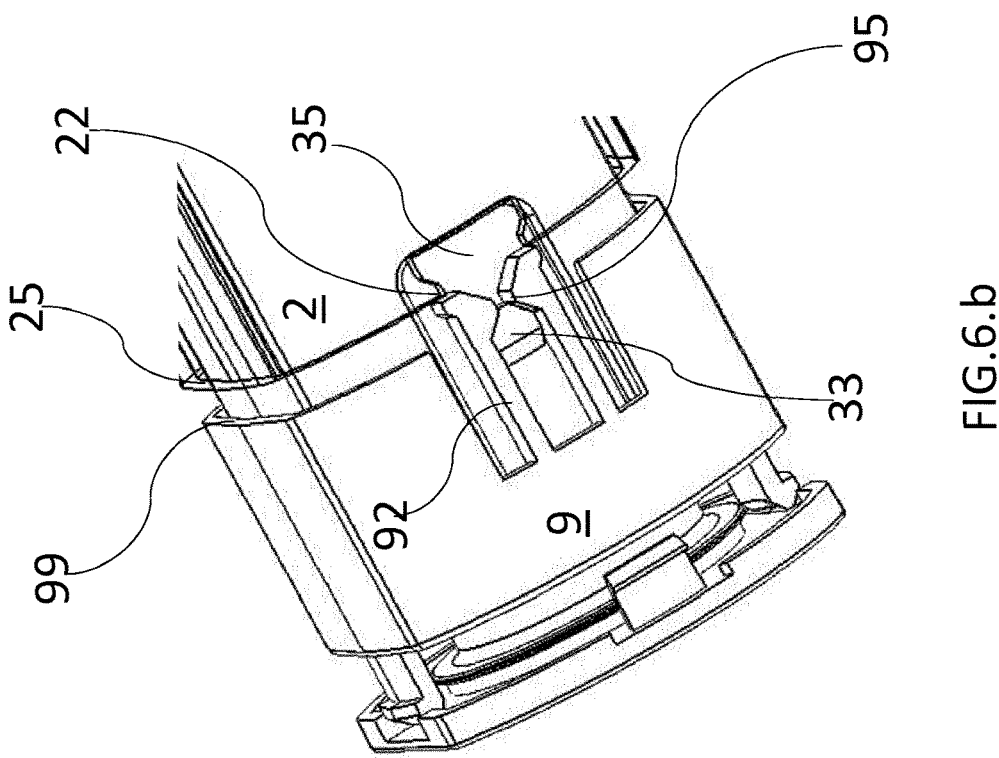
FIG.6.b
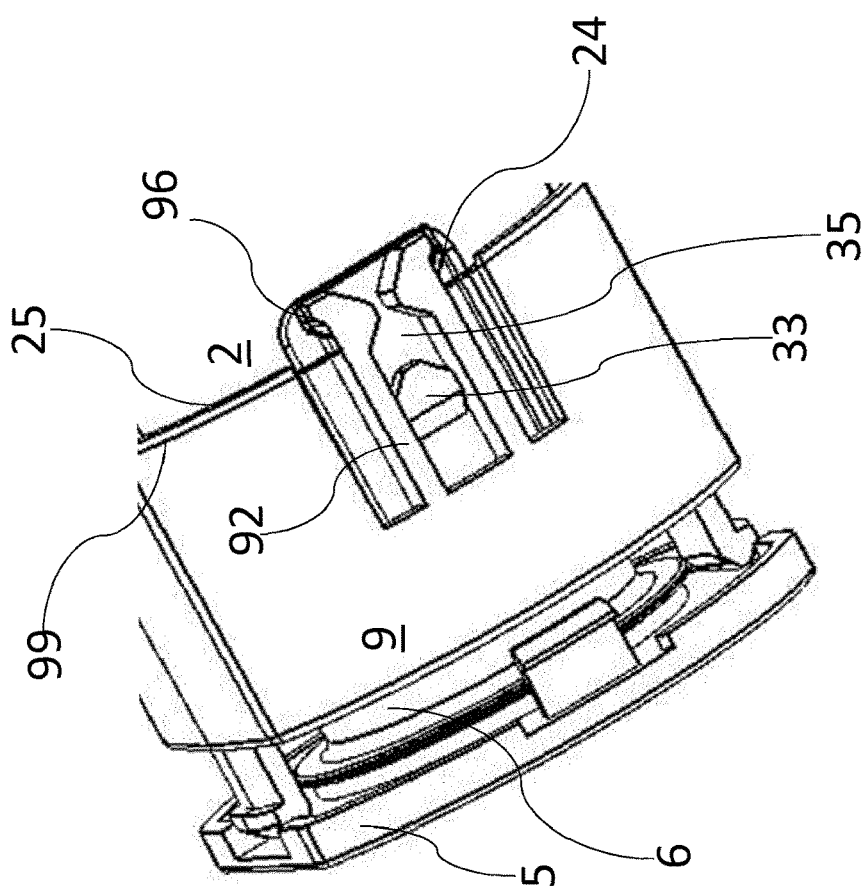
FIG.6.a
FIG.6

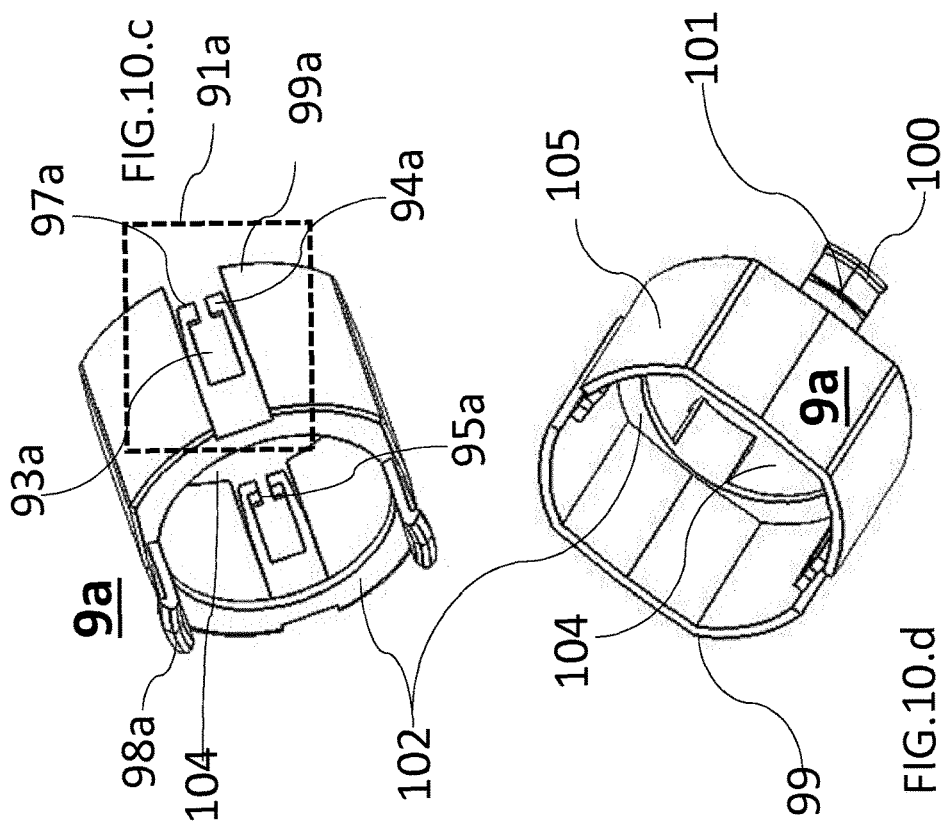
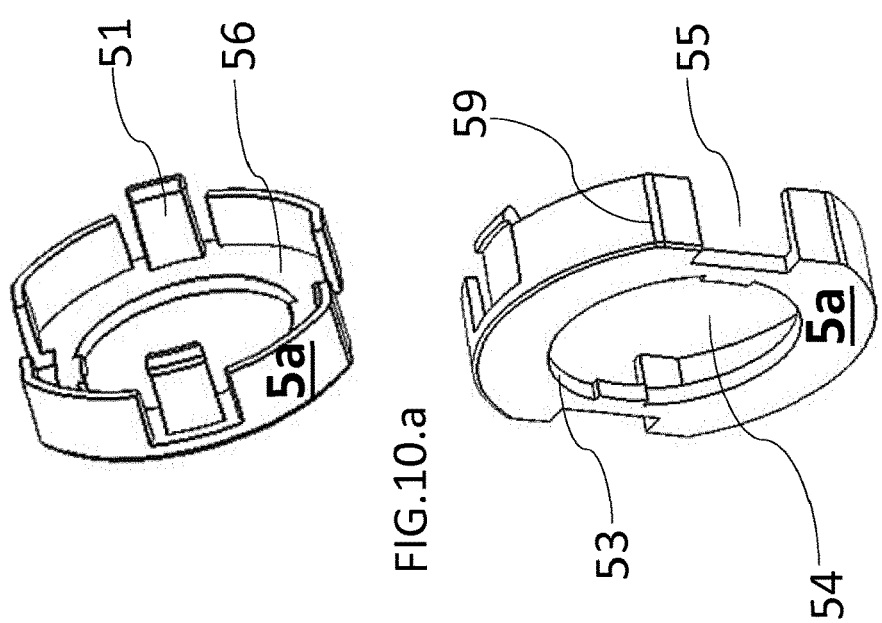

FIG.12
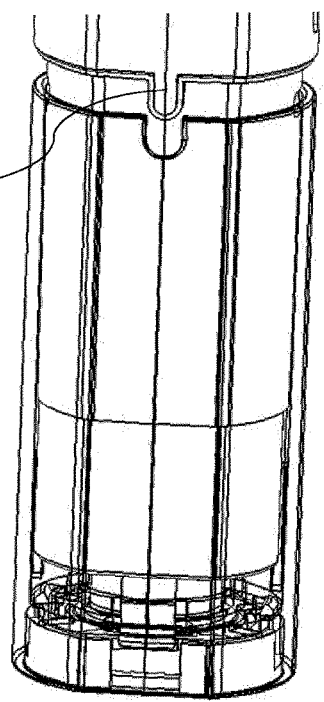
FIG.12.c
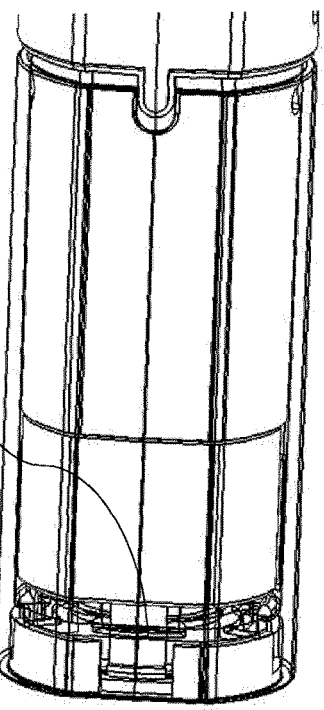
FIG.12.d
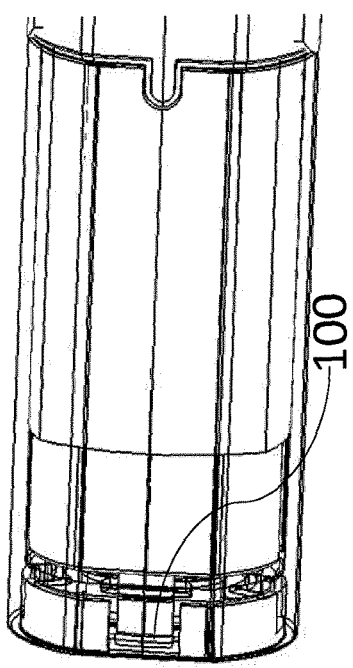
FIG.12.a
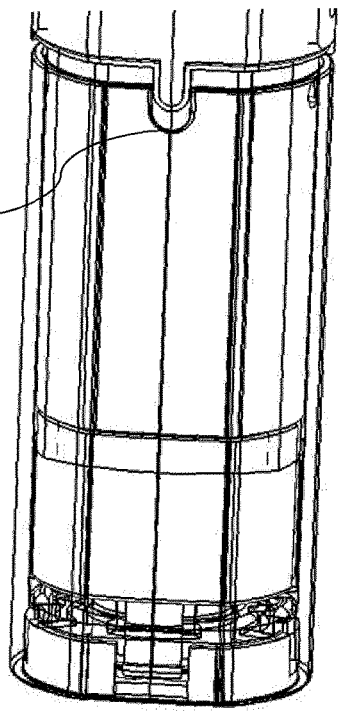
FIG.12.b

MEDICAMENT DELIVERY DEVICE HAVING A CAP ASSEMBLY

CROSS REFERENCE TO RELATED APPLICATIONS

The present application is a U.S. National Phase Application pursuant to 35 U.S.C. § 371 of International Application No. PCT/EP2017/076495 filed Oct. 17, 2017, which claims priority to European Patent Application No. 16195281.7 filed Oct. 24, 2016. The entire disclosure contents of these applications are hereby incorporated by reference into the present application.

TECHNICAL FIELD

The present disclosure generally relates to medicament delivery devices. In particular, it relates to a medicament delivery device having a removable cap assembly that prevents the medicament delivery device to be accidentally activated and that prevents a recapping.

BACKGROUND

Medicament delivery devices, such as injectors, auto-injectors and inhalers, typically comprise a housing in which a medicament container containing a medicament is to be arranged. Upon activation of the medicament delivery device, the medicament is expelled through a medicament delivery member, as for example a needle or a nozzle.

In injection devices where the medicament delivery member is a needle, said needle is protected and kept sterile. Thus, the medicament delivery member may be provided with a delivery member shield, or sheath, such as a Flexible Needle Shield (FNS) or a Rigid Needle Shield (RNS). The delivery member shield may thus be attached to the medicament container to cover the medicament delivery member.

More specifically, auto-injectors normally comprise an actuation mechanism for exerting a force to expel the medicament from the medicament container through the medicament delivery member, an activation member which may be coupled to the actuation mechanism for releasing the actuation mechanism to expel the medicament, and a cap connected to the front end of the housing for removing the delivery member shield. Some auto-injectors, as disclosed in WO2014131858 A1, also comprise a mechanical interlock which prevents actuation of the activation member prior to removal of the cap such that when the cap is removed, the mechanical interlock then allows the actuation of the activation member.

Further, EP2745866A1 discloses also an auto-injector which comprises a housing for containing a syringe with a needle, a force mechanism for applying a force to eject a liquid medicine from the syringe, a biased needle cover sleeve coupled to the force mechanism for releasing the force mechanism to cause an injection and having a flexible arm, a needle shield covering the needle, a cap connected to the front end of the housing for removing the needle shield. When the cap is attached to the housing, the needle cover sleeve is partially moved into the housing such that the flexible arm is deflected by a surface of the cap and kept in the deflected state by a surface of the housing such that actuation of the needle cover sleeve is prevented prior to removal of the cap. When the cap is removed, the needle cover is partially moved out from the housing such that flexible arm does not interact with the housing and allows the actuation of the needle cover sleeve.

SUMMARY

In view of the known prior art, it is noticed that a removable cap assembly has the function of providing mechanical protection to the medicament delivery member while attached to the housing and to remove the delivery member shield when part of the cap assembly is removed from the housing.

However, there is a tangible risk that, the activation mechanism of the medicament delivery device may be influenced by any accidental or deliberate movement on the activation member during transportation or by accidentally dropping the medicament delivery device among others.

Thus, a general object of the present disclosure is to provide a medicament delivery device having a simple and robust cap assembly having a common feature in the form of an integrity lock which prevents the medicament delivery device to be accidentally activated and that also prevents a recapping which gives an indication to the user that the device has been used or that the sterility of the medicament delivery member has been compromised.

There is hence according to a first aspect of the present disclosure to provide a medicament delivery device according to the features in the present claims 1-17.

BRIEF DESCRIPTION OF THE DRAWINGS

The specific embodiments of the inventive concept will now be described, by way of example, with reference to the accompanying drawings, in which:

FIG. 6 illustrates a closer view of the first and second positions (FIG. 6a and FIG. 6.b) in the first embodiment of FIG. 1.

FIG. 10 shows side views of on components of the second embodiment of FIG. 8, namely the cap lock (FIG. 10a, FIG. 10b) and the integration lock member (FIG. 10c, FIG. 10d) disclosing minor changes compared with the first embodiment of FIG. 1

FIG. 12 shows transparent views of the proximal part of the medicament delivery device according to the sequence from the first position to the second position.

DETAILED DESCRIPTION

There will now be described with reference to FIGS. 1 to 10 of the accompanying drawings, according to the device of the present invention.

In the present application, when the term "distal part/end" is used, this refers to the part/end of delivery device, or the parts/ends of the members thereof, which is/are located the furthest away from the medicament delivery site of the patient. Correspondingly, when the term "proximal part/end" is used, this refers to the part/end of delivery device, or the parts/ends of the members thereof, which is/are located closest from the medicament delivery site of the patient.

Figure 1:
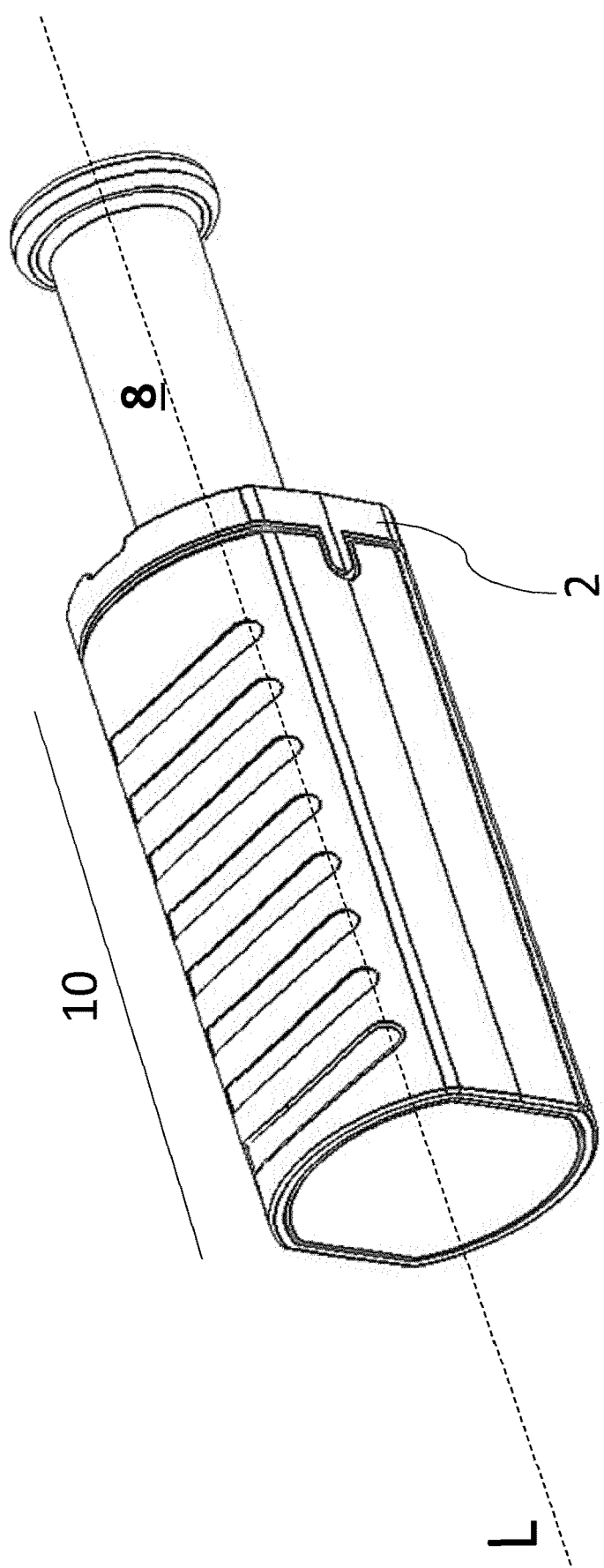
FIG. 1 illustrates a perspective view along the longitudinal L-axis of the cap assembly of the medicament delivery device according to a first embodiment of the present invention.

Parts of a medicament delivery device according to the present invention are illustrated in FIG. 1. It is shown a housing 2 having a proximal end and a distal end. The housing 2 extends along a longitudinal L-axis. It is also shown a removable cap assembly 10 and a medicament container 8.

Figure 2:
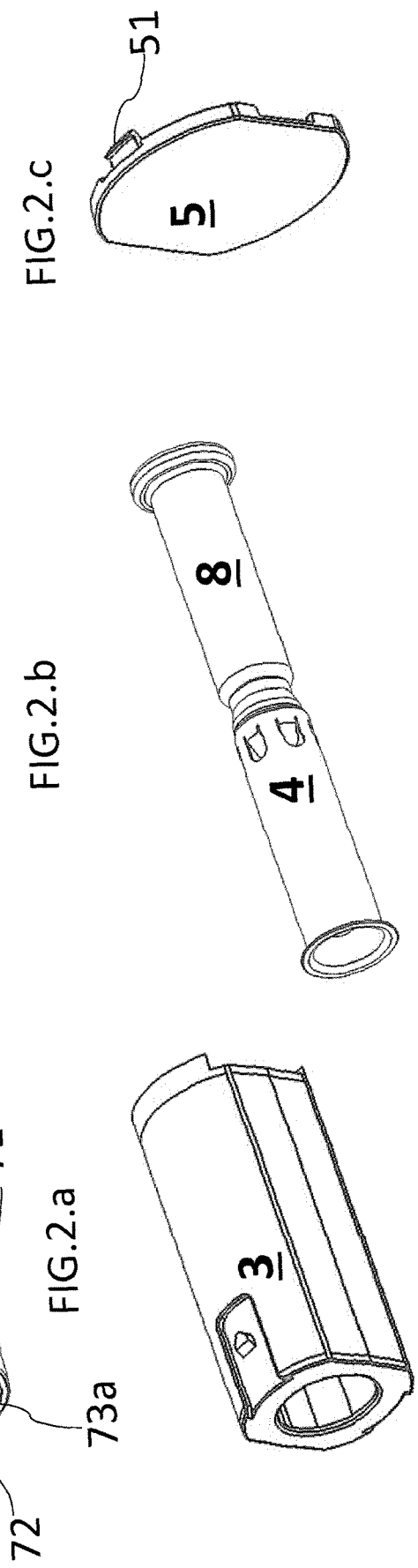
FIG. 2 shows an exploded perspective view of the embodiment disclosed by FIG. 1, wherein its parts are depicted in more detail.

FIG. 2 illustrates an exploded view of a preferred embodiment of the invention according to FIG. 1. The figure depicts a more detailed view of the removable cap assembly 10 which comprises a cap closer 5 (FIG. 2.*f*), an outer tubular cap body 7 (FIG. 2.*a*) and an inner tubular integrity lock member 9 (FIG. 2.*b*). It also depicts a tubular housing 2 (FIG. 2.*c*) and an activation member 3 (FIG. 2.*d*). Both the tubular housing 2 and the activation member 3 being parts of the medicament delivery device and of the cap assembly. Further, it also depicts a deshielder 4 connected to a medicament container 8 (FIG. 2.*e*).

The outer tubular cap body 7 (FIG. 2.*a*) is removably connected to the tubular housing 2 along the L-axis as previously shown in FIG. 1. Further, the outer tubular cap body 7 comprises gripping elements 75 on its outer surface (also visible in FIG. 1), and a transversal wall 72 having an opening channel 71 for allowing the distal part of the deshielder 4 to pass through during the assembly. The gripping elements 75 facilitate an enhanced grip by the fingers/hands of a user on the outer tubular cap body 7.

The inner tubular integrity lock member 9 (FIG. 2.*b*) is coaxially coupled to the outer tubular cap body 7 at its proximal part for the purpose of facilitating the assembly. The transversal wall 72 of the outer tubular cap body 7 comprises a pair of spaced apart and opposite openings 73*a* and wherein each opening 73*a* is configured to receive a snap fit member 51 of the cap closer 5 (FIG. 2.*f*) and thereby fixedly connect the outer tubular cap body 7 and the cap closer 5.

The activation member 3 (FIG. 2.*d*) is operably connected to a medicament delivery device mechanism (not shown) which is associated with the medicament container, and said activation member 3 is longitudinally movable in relation to the tubular housing 2 from an extended position to a retracted position for activating the medicament delivery mechanism. In the extended position, a proximal portion of the activation member 3 extends from the proximal end of the housing 2 and in the retracted position most of the proximal portion of the activation member 3 is covered by the tubular housing 2 or the proximal end surface of the activation member 3 is flush with the proximal end surface of the housing 2.

Figure 3:
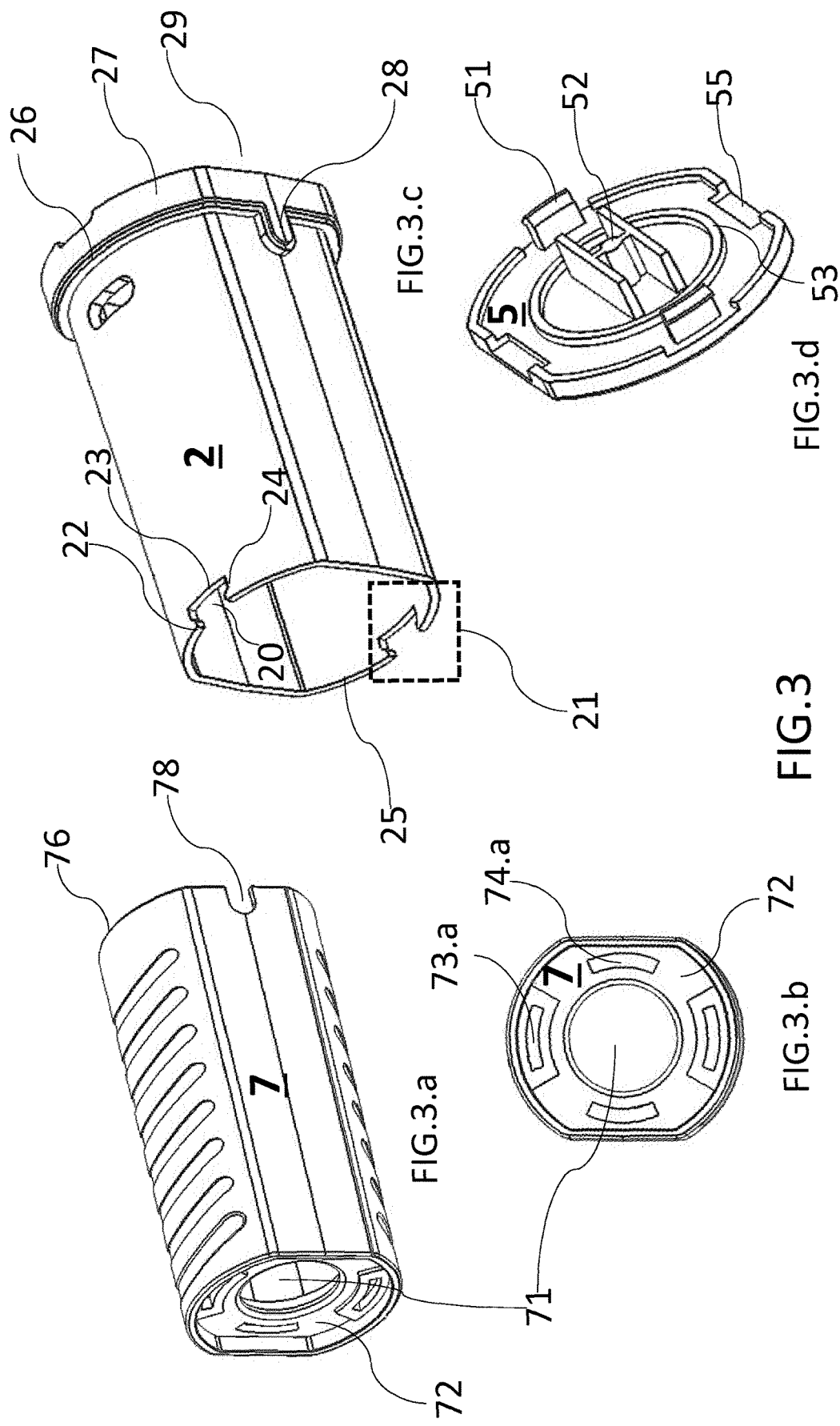
FIG. 3 shows side views of selected components of the embodiment of FIG. 1: the tubular cap body (FIGS. 3a, 3b), the housing (FIG. 3c) and the cap closer (FIG. 3d).

FIG. 3 shows in more detail the tubular cap body 7 (FIG. 3.*a*), a lateral view of the transversal wall 72 of the tubular cap body 7 (FIG. 3.*b*), the tubular housing 2 (FIG. 3.*c*) and the inner face view of the cap closer 5 (FIG. 3.*d*) according to the embodiment of FIG. 1.

The outer tubular cap body 7 (FIG. 3.*a*) further comprises at its distal end a distal rim 76 and a receiving tab portion 78 which is part of the distal rim 76.

The transversal wall 72 of the tubular cap body 7 (FIG. 3.*b*) comprises: the opening channel 71 and four radial openings 73, 74. The two opposed openings (73*a*,73*b*) (73*b* not shown in FIG. 3.*b*) engages respectively to the snap fit members 51 of the cap closer 5 securing the cap closer 5 to the tubular cap body 7. Conversely, the other two opposed openings (74*a*,74*b*) (74*b* not shown in FIG. 3.*b*) engages likewise to flaps 98 of the inner tubular integrity lock member 9 (FIG. 4.*b*) to fix the integral locking member 9 to the tubular cap body 7.

The tubular housing 2 (FIG. 3.*c*) distal part end 29 comprises an annular collar 27. The annular collar 27 of the housing 2 comprises a proximal radial edge 26 with two proximal prolongations in the form of two semi-circular tabs 28 at opposite sides of the tubular housing 2, which dock respectively with the receiving portions 78 of the outer tubular cap body 7. Alternatively, the annular collar 27 of the housing 2 may comprise cavities which dock respectively with tabs of the outer tubular cap body 7.

The tubular housing 2 proximal part comprises a proximal rim 25 with two opposed second engaging structures 21. Each second engaging structure 21 is formed as a U shaped slot or cut-out 20, which in turn is defined by a transversal edge 23 and two spaced apart and opposite side edges 24. Each side edge 24 forms a transversal inwardly protrusion which presents an edge 22 and wherein said edge 22 forms part of the proximal rim 25 of the tubular housing 2

The cap closer 5 proximal side is depicted in FIG. 2.*f*, hence a distal view or opposite side of the cap closer is required (FIG. 3.*d*). As it can be seen, an "H" leg elevation 52 of the cap closer 5 docks on the channel opening 71 of the transversal wall 72 of the tubular cap body 7. The cap closer 5 also comprises an inner circular ledge 53, the function of which will be explained below.

Figure 4:
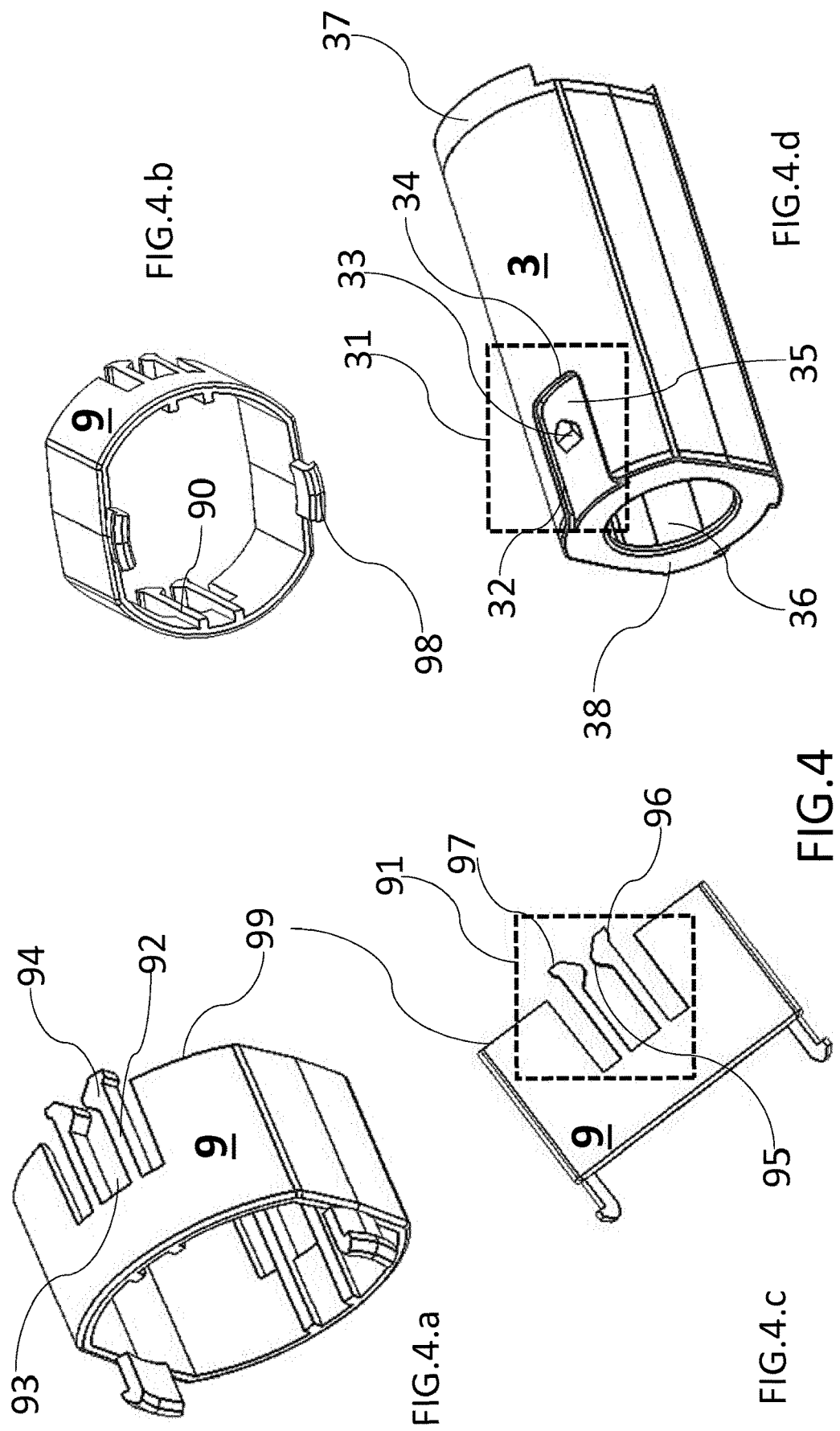
FIG. 4 shows side views of two main components of the embodiment of FIG. 1: the integration lock member (FIGS. 4a, 4b, 4c) and the activation member (FIG. 4d).

FIG. 4 shows the integration lock member 9 in a perspective proximal view (FIG. 4.*a*), a corresponding distal view (FIG. 4.*b*) and its lateral view (FIG. 4.*c*). Additionally, a perspective view of the activation member 3 is provided (FIG. 4.*d*).

The inner tubular integrity lock member 9 (FIG. 4.*a*) comprises at is distal end a distal rim 99 and a resilient structure 91, which is formed by a pair of spaced apart longitudinally extending arms 92 distally extending from a U-shaped cut-out portion. The pair of spaced apart longitudinally extending arms 92 extends a certain distance from the distal rim 99 of the inner tubular integrity lock member 9 and such extending arms 92 run distally as two distal free ends 94. Further, the spaced apart longitudinally extending arms 92 are flexible in the transversal direction and define an opening or central cut-out 93 between them.

As seen on FIG. 4.*b*, each longitudinally extending arm 92 extends radially inwards from the inner surface of the inner tubular integrity lock member 9 and can be seen as an elevation or internal rib 90. Further, each distal free end 94 has a first transversal inwardly extending lip 95, a second transversal outwardly extending lip 96 and a distal top edge 97 (FIG. 4.c).

The activation member 3 proximal portion presents two opposed radial outer surfaces (FIG. 4.d), each surface forming a first engaging structure 31. The first engaging structure 31 comprises a guiding recess and a guiding protrusion 33. The guiding recess is U-shaped and it is defined by two parallel longitudinally extending side walls 32, a transversal side wall 34 and a bottom wall 35. The guiding protrusion 33 is arranged on the outer surface of the bottom wall 35 of the guiding recess.

Furthermore, the activation member 3 comprises a transversal wall 38 at its proximal end and has an opening channel 36 for allowing the deshielder 4 to pass through.

FIG. 4.d also shows two spaced apart and opposite wings 37 extending from the distal rim of the activation member 3 distal end. Said opposite wings 37 may be configured to interact with the medicament delivery mechanism (not shown) of the medicament delivery device.

Each second transversal outwardly extending lip 96 has a shape configured to interact with a corresponding shape formed in each side edge 24 of the U-shaped slot or cut-out 20 of the housing 2 for allowing a distal portion of each longitudinally extending arm 92 to flex transversally inward and each first transversal inwardly extending lip 95 has a shape configured to interact with a corresponding shape of the guiding protrusion 33 arranged on the bottom wall 35 of the guiding recess for allowing the longitudinally extending arm 92 to flex transversally outward when the inner tubular integrity lock member 9 is proximally displaced a certain distance in relation to the housing 2 and to the activation member 3.

Figure 5:
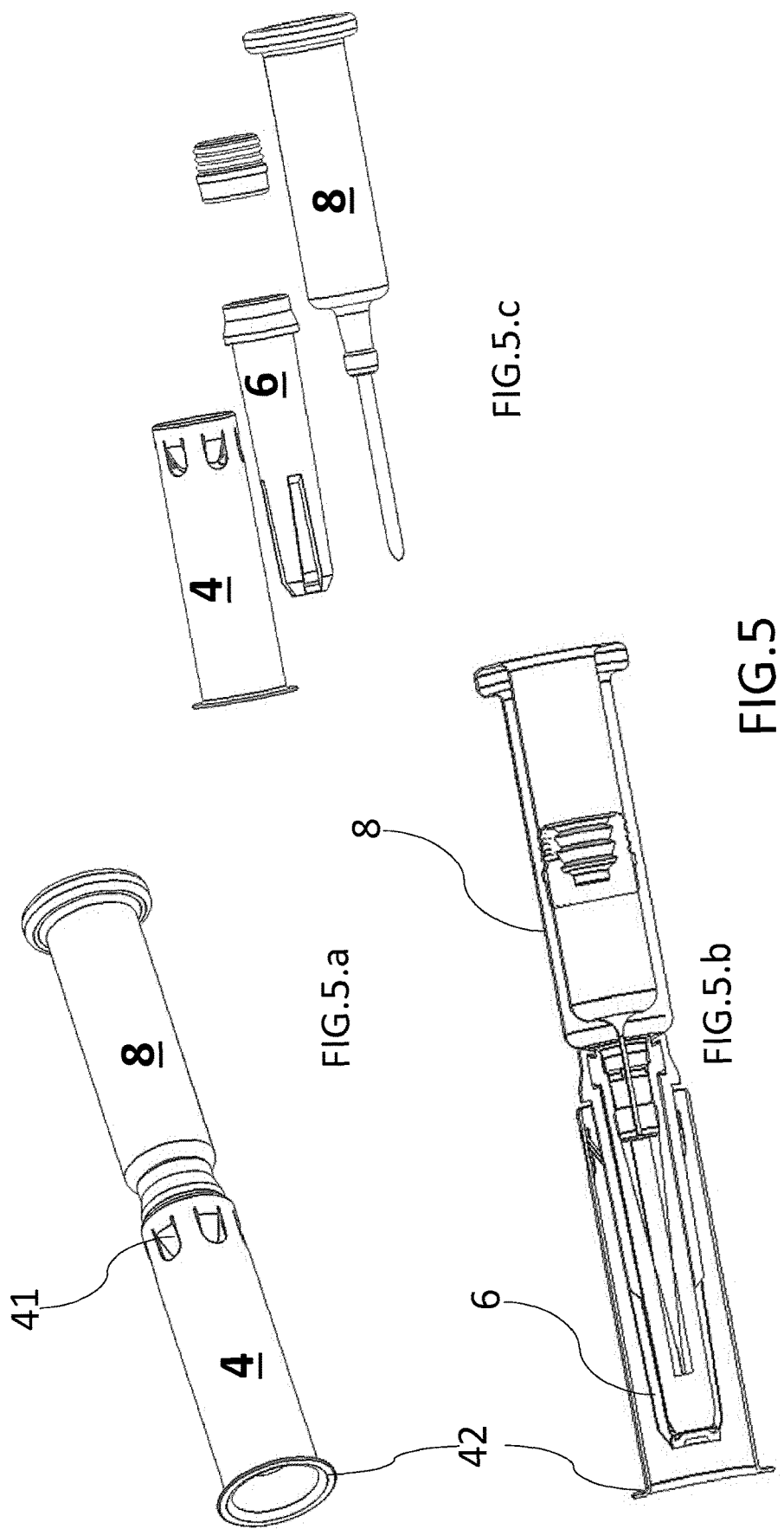
FIG. 5 illustrates a perspective and cross-sectional view of the internal parts of the embodiment of FIG. 1, particularly the deshielder connected to the medicament container.

FIG. 5 illustrates a side view, a cross-sectional view and an exploded view (FIG. 5.c) of the deshielder 4 connected to a medicament delivery member shield 6 through connecting members 41 (FIG. 5.a). The medicament delivery member shield 6 in the present first embodiment is shown as a Rigid Needle Shield (RNS) but it may also be a Flexible Needle Shield (RNS) (FIG. 5.b). The FNS is connected to the medicament container 8 for protecting a medicament delivery member which in the present embodiment is shown as a needle. The deshielder 4 comprises a proximal end part with a radially extending outward rim 42. This rim 42 is configured to be positioned between the inner circular ledge 53 of the cap closer 5 and the transversal wall 72 of the outer tubular cap body 7, such that it is fixedly attached to the outer tubular cap body 7.

In FIG. 6, lateral views of the proximal portion of the removable cap assembly 10 (FIG. 6.a and FIG. 6.b) in a first and a second position can be observed particularly for the first embodiment according to FIG. 1.

The removable cap assembly 10 is configured to be proximally moved in relation to the housing 2 and in relation to the activation member 3 from a first position to a second position. In the first position (FIG. 6.a) of the 30o removable cap assembly 10, the resilient structure 91 of the inner tubular integrity lock member 9 is removably engaged in a pocket defined by a portion of the first engaging structure 31 of the activation member 3 and a portion of the second engaging structure 21 of the housing 2 for preventing the activation member 3 from moving into the retracted position.

Thus, when the removable cap assembly 10 is in the first position (FIG. 6.a), the pair of spaced apart longitudinally extending arms 92 extend longitudinally along the bottom wall 35 of the U-shaped guiding recess and receive the guiding protrusion 33, arranged on the bottom wall 35 of the U-shaped guiding recess, in the opening 93 defined by the pair of spaced apart longitudinally extending arms 92, and each second transversal outwardly extending lip 96 is releasably connected to the corresponding side edge 24 of the U-shaped slot or cut-out 20 of the housing 2 for preventing the longitudinally extending arms 92 to flex transversally outwards. Further, when the removable cap assembly 10 is in the first position, the proximal rim 25 of the housing 2 bears against the distal rim 99 of the inner tubular integrity lock member 9 and the proximal radial edge 26 of the housing 2 bears against the distal rim 76 of the tubular cap body 7. Also, when the removable cap assembly 10 is in the first position, the medicament delivery member shield 6, i.e. the RNS, is attached to medicament container 8, i.e. a syringe and thereby maintaining the sterility of the medicament delivery member, i.e. the needle, and the connecting members 41 of the deshielder 4 are connected to the RNS.

Figure 7:
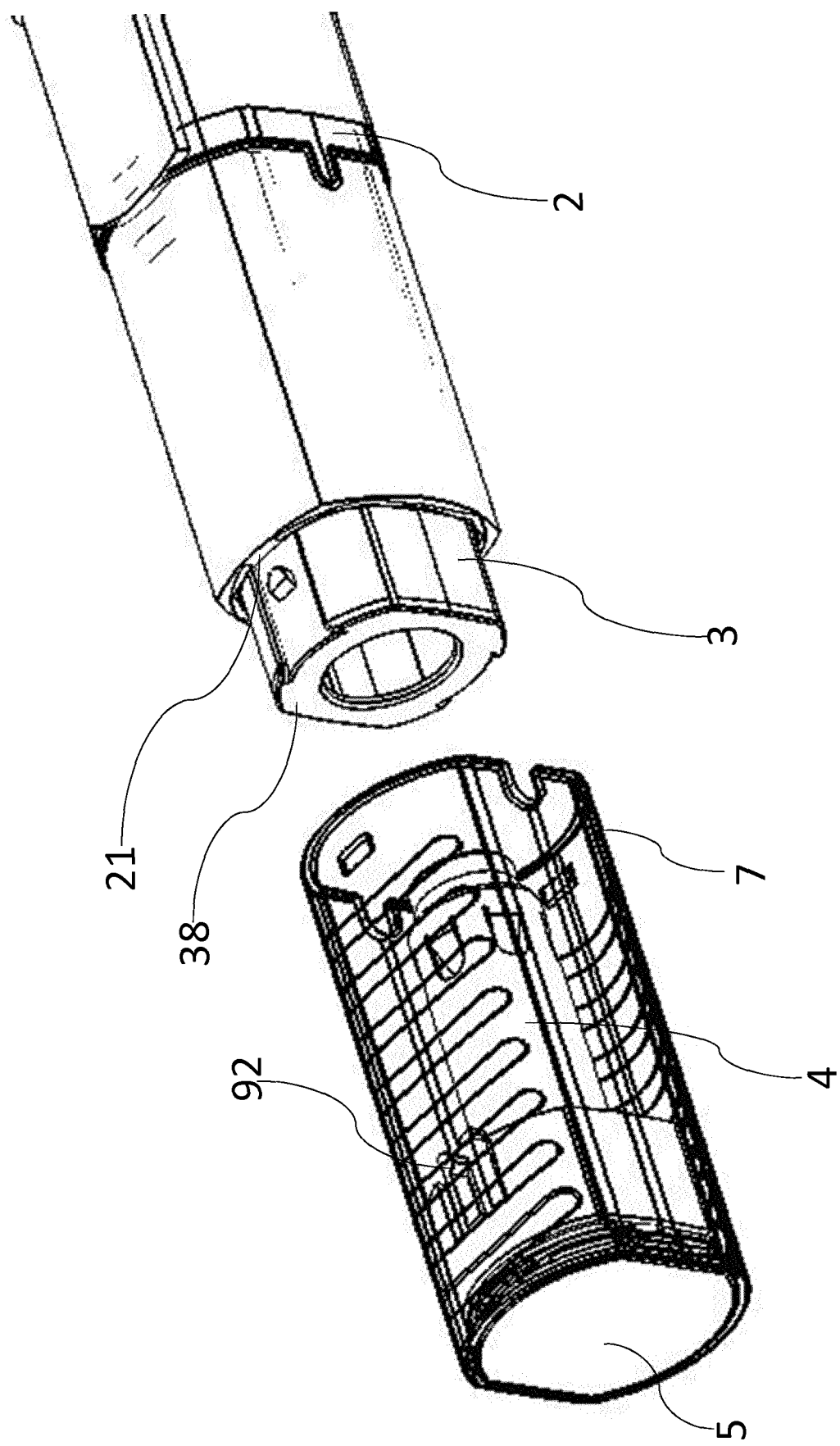
FIG. 7. shows the medicament delivery device in the position of "cap off", when the removable cap assembly is totally pulled out by the user.

According to FIG. 7, the user draws out manually the outer tubular cap body 7 along the L-axis. Such movement separates the removable cap assembly 10 from the tubular housing 2 and from the activation member 3. At the same time the deshielder 4 together with the medicament delivery member shield 6 is separated from the syringe body 8 and exposes the delivery member 6 i.e. the needle which is surrounded by the activation member 3. The separation of the removable cap assembly 10 from the tubular housing 2 and from the activation member 3 occurs when the free ends 94 of the longitudinally extending arms 92 are disengaged from the pocket formed by the portions of the first 31 and the second 21 engaging structures due to the flexibility of the free ends 94 of the longitudinally extending arms 92.

Moreover, when the removable cap assembly 10 is in the second position (FIG. 6.b), the pair of spaced apart longitudinally extending arms 92 extend longitudinally along the bottom wall 35 of the U-shaped guiding recess and each first transversal inwardly extending lip 95 bears against the guiding protrusion 33, and each distal top edge 97 of the arms 92 bears against the edge 22 of the proximal rim 25 of the housing 2 for preventing the removable cap assembly from moving into the first position i.e. a recapping. Further, when the removable cap assembly 10 is in the second position, the proximal rim 25 of the housing 2 is positioned at a certain distance from the distal rim 99 of the inner tubular integrity lock member 9 and the proximal radial edge 26 of the housing 2 is positioned at a certain distance from the distal rim 76 of the tubular cap body 7. Also, when the removable cap assembly 10 is in the second position, the medicament delivery member shield 6, i.e. the RNS, has moved distally a certain distance in relation to medicament container 8, i.e. a syringe and the connecting members 41 of the deshielder 4 are still connected to the RNS. The pocket formed by the portions of the second 21 and first 31 engaging structures is thus unreachable by the free ends 94 of the extending arms 92. Since the removable cap assembly 10 is prevented from moving into the first position (FIG. 6.b), the distance between the proximal radial edge 26 of the tubular housing 2 and the distal rim 76 of the tubular cap body 7 gives an indication to a user that the sterility of the medicament delivery member, i.e. the needle, has been compromised and/or that the device has been used. It gives a tamper-proof indication to the user.

Figure 8:
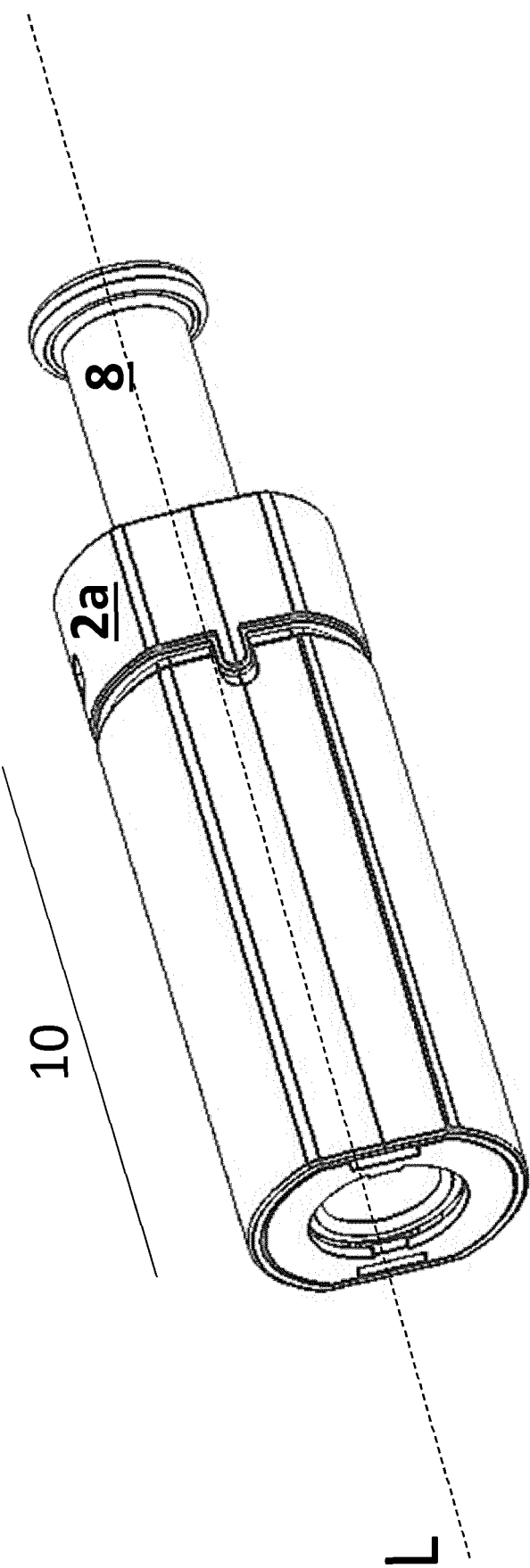
FIG. 8. depicts a second embodiment of the invention along the longitudinal L-axis.

FIG. 8 illustrates, in perspective, parts of a medicament delivery device 1 of the invention along the longitudinal L-axis in a second embodiment of the medicament delivery device 1 of the invention. Though the tubular cap body 7a (not shown in FIG. 8) lacks the gripping elements 75, they may still be implemented as an alternative feature.

Figure 9:
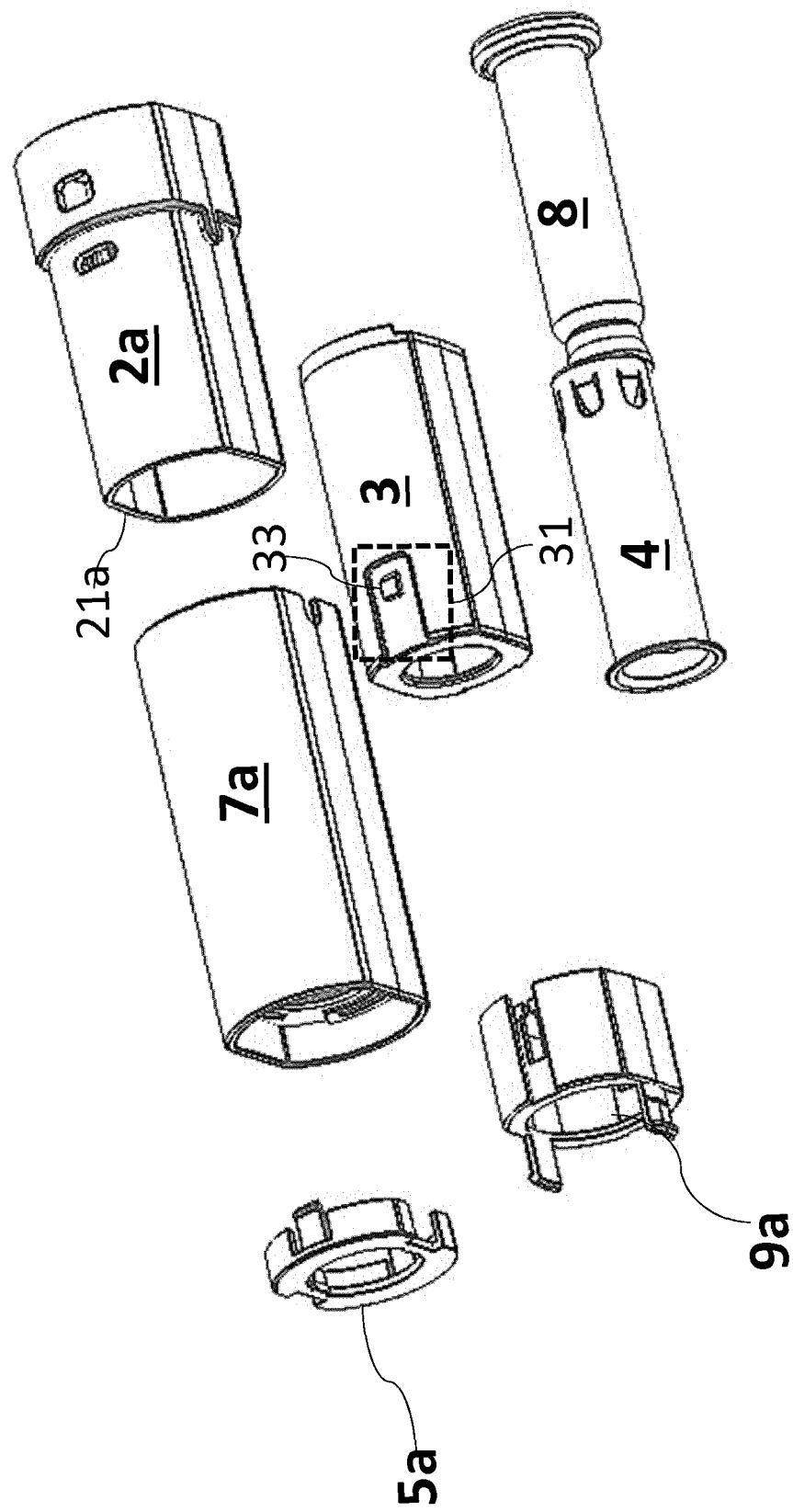
FIG. 9 shows an exploded view of the second embodiment disclosed by FIG. 7, with notably the lack of a second engaging structure on the tubular housing compared with the first embodiment of FIG. 1.

FIG. 9 illustrates an exploded view of the second embodiment of the invention according to FIG. 8. FIG. 10 depicts a more detailed view of the key parts of the device similar to FIG. 2. Albeit the parts are similar in both embodiments, there are some minor differences on the second embodiment, namely: the tubular housing 2a, the cap closer 5a, the outer tubular cap body 7a and the inner tubular integrity lock member 9a FIG. 10 shows in more details the perspective views of the cap closer 5a (FIG. 10.a and FIG. 10.b) and the inner tubular integrity lock member 9a (FIG. 10.c and FIG. 10.d), according to the second embodiment of the FIG. 8.

The cap closer 5a may be open or close depending on the needs for assembly of the medicament delivery device 1. In the second embodiment (FIG. 10.a), the cap closer 5a comprises a transversal wall 56 having an opening channel 54, snap fit members 51 and longitudinally extending wall portions 59. The snap fit members 51 and the longitudinally extending wall portions 59 extend distally from the transversal wall 56. The cap closer 5a further comprises receiving tab portions 55 arranged between the longitudinally extending wall portions 59 (FIG. 10.b). The longitudinally extending wall portions 59 dock with the inner surface at the proximal part of the outer tubular cap body 7a.

As it can be seen (FIG. 9 and FIG. 10.c) the inner tubular integrity lock member 9a has been slightly modified. The inner tubular integrity lock member 9a comprises a transversal wall 102 having a through opening 104, and longitudinally extending tubular walls 105 having spaced apart and opposite cut-outs. The longitudinally extending tubular walls 105 and the spaced apart and opposite longitudinally extending arms 92a (not shown in FIG. 10.c) extend distally from the transversal wall 102 and are radial offset in relation to each other wherein the spaced apart and opposite longitudinally extending arms 92a are closer to the axis L. The spaced arms 92a are flexible in the transversal direction and define an opening or central cut-out 93a between them similar to the one in the first embodiment. Each of the longitudinally extending arms 92a of the inner tubular integrity lock member 9a (FIG. 10.c) is also provided with a distal free end 94a having a first transversal inwardly extending lip 95a and a distal top edge 97a. However, the distal rim 99a of the distal end of the integrity lock member 9a has been prolonged such that there is certain distance between the distal top edges 97a of the longitudinally extending arms 92a and the distal rim 99a of the distal end of the integrity lock member 9a. Thus, the resilient structure 91a still comprises the pair of spaced apart and opposite longitudinally extending arms 92a and the distal rim 99a. This resilient structure 91a of the inner tubular integrity lock member 9a has been modified in order to achieve an improved cooperation with the first engaging structure 31 of the activation member 3 and the second engaging structure 21a of the housing 2.

The proximal end of inner tubular integrity lock member 9a includes two equal lateral flaps 98a which extends proximally from the transversal wall 102 (FIG. 10.d). Each flap 98a comprises a snap fit member configured to be connected to a corresponding second opening 74a, 74b of the transversal wall 72 of the tubular cap body 7a. Further, each flap 98 is enlarged towards the proximal end forming a first outer protrusion 100. Also each flap 98 is provided with a second outer protrusion 101 which has a distally inclined surface and a proximal step surface. The flaps 98a of the inner tubular integrity lock member 9a pass through the second openings 74a, 74b of the transversal wall 72 of the tubular cap body 7a such that the inner tubular integrity lock member 9a is longitudinally movable within certain distance in relation to the tubular cap body 7a.

Figure 11:
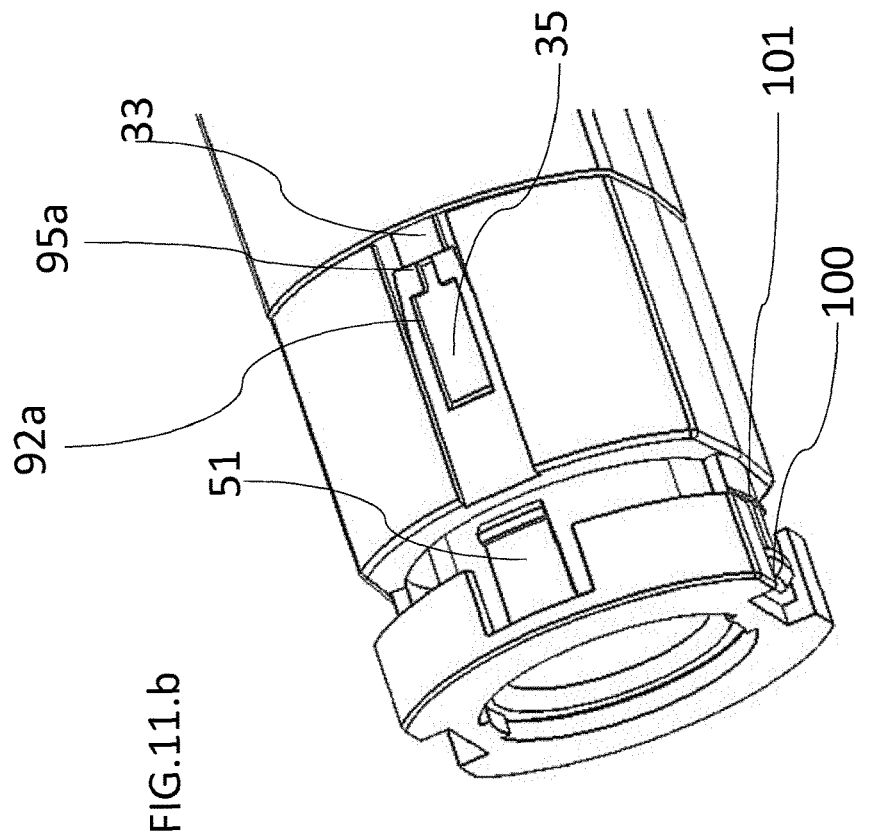
FIG. 11 illustrates in two different positions (FIG. 11.*a*, FIG. 11.*b*) a first position and a second position similar to the first embodiment.

Lateral views of the first and second position of the removable cap assembly 10 can be observed in FIG. 11.

As mentioned above, the activation member 3 is longitudinally movable in relation to the tubular housing 2 from an extended position to a retracted position for activating the medicament delivery 1 mechanism. In the extended position, a proximal portion of the activation member 3 extends from the proximal end of the housing 2 and in the retracted position most of the proximal portion of the activation member 3 is covered by the tubular 30o housing 2 or the proximal end surface of the activation member 3 is flush with the proximal end surface of the housing 2a.

In a first position of the removable cap assembly 10, the resilient structure 91a of the inner tubular integrity lock member 9a is engaged to a first engaging structure 31 of the activation member 3 and to a second engaging structure 21a of the housing 2 in order to prevent the activation member 3 from moving into the retracted position in case that the device is accidentally dropped or activated during transportation.

More particularly, in the first position of the removable cap assembly (FIG. 11.a), the free ends 94a of the extending arms 92a are removably attached in a pocket defined by a portion of the first engaging structure 31 and the second engaging structure 21a wherein the distal top edges 97a of the longitudinally extending arms 92a bears against the transversal side wall 34 and are placed at certain distance from the second engaging structure 21a which in the second embodiment is the proximal rim of the housing 2a.

Further, in the first position (FIG. 11.a), the second engaging structure 21a of the housing 2a also bears against the distal rim 99a of the inner tubular integrity lock member 9a. Further, the pair of spaced apart longitudinally extending arms 92a extend longitudinally onto the bottom wall 35 of the U-shaped guiding recess and receive the guiding protrusion 33, which is arranged on the bottom wall 35 of the U-shaped guiding recess of the activation member 3, in the opening 93a defined by the pair of spaced apart longitudinally extending arms 92a and the first transversal inwardly extending lips 95a. Moreover, in the first position of the removable cap assembly 10, each proximal portion of the flaps 98a of the integrity lock member 9a is positioned in a corresponding receiving tab portion 55 of the cap closer 5 such that the proximal portion of the flaps 98 are movable radially inwards in relation to the cap closer 5; and each distally inclined surface of the second outer protrusions 101 of the flaps 98a of the integrity lock member 9a bears against a corresponding surface surrounding the opening 74 of the transversal wall 72 of the tubular cap body 7a. Further, the first outer protrusion 100 and the rim 42 of the deshielder 4 are positioned at certain distance from the transversal wall 72 of the tubular cap body 7a.

The user draws out manually the proximal portion of the medicament delivery device 1 when handling the outer tubular cap body 7a along the L-axis in ways similar to the first embodiment. Such movement separates the removable cap assembly 10 from the tubular housing 2a and from the activation member 3. At the same time the deshielder 4 together with the medicament delivery member shield 6 is separated from the syringe body 8 and exposes the delivery member 6 i.e. the needle which is surrounded by the activation member 3.

The separation occurs in several steps, from the first position (FIG. 11.a) to a second position (FIG. 11.b):

The outer tubular cap body 7a together with the cap closer 5a is scarcely moved in relation to the inner tubular integrity lock member 9a and to the housing 2a along the L-axis towards the proximal end, wherein the surfaces surrounding the openings 74 of the transversal wall 72 of the tubular cap body 7a interact with distal inclined surfaces of the second outer protrusions 101 of the flaps 98a of the integrity lock member 9 such that the flaps 98a flex radially inwards and after the surfaces surrounding the openings 74 of the transversal wall 72 has passed the distally inclined surfaces of the second outer protrusions 101, the flaps 98a flex back to its original position.

The outer tubular cap body 7a together with the cap closer 5a is further moved in relation to the inner tubular integrity lock member 9a and to the housing 2a along the L-axis towards the proximal end until the first outer protrusion 100 bears against the transversal wall 72 of the tubular cap body 7a. At this stage, the rim 42 of the deshielder 4 also bears against the transversal wall 72 of the outer tubular cap body 7a.

The integrity lock member 9a, the deshielder 4 and the medicament delivery member shield 6 together with the outer tubular cap body 7a, can now be moved in relation to the housing 2a towards the proximal end wherein the distal free-ends 94a of the longitudinally extending arms 92a overcome the protrusion 33 when sliding against the bottom wall 35 and the edges of the protrusion 33 of the activation member 3 such that the distal free-ends 94a of the longitudinally extending arms 92a are liberated from the pocket formed by the engaging structure 31 of the activation member 3 and the second engaging structure 21a.

At this stage the user may try to recap the removable cap assembly 10 by moving the outer tubular cap body 7a in relation to the housing 2a towards the distal end. After performing this movement, the removable cap assembly 10 is (FIG. 11.b) in the second position wherein the pair of spaced apart longitudinally extending arms 92a extend longitudinally onto the bottom wall 35 of the U-shaped guiding recess and each distal top edge 97a of the arms 92a bears against an step surface of the guiding protrusion 33 of the activation member 3 wherein the activation member 3 is moved a certain distance towards the distal end in relation to the housing 2a until the distal rim 99a of the distal end of the integrity lock member 9a bears against the second engaging member 21a of the housing 2a. The movement of the activation member 3 towards the distal end does not trigger the actuation mechanism. Also, the surfaces surrounding the openings 74 of the transversal wall 72 of the tubular cap body 7 bear against the proximal step surfaces of the second outer protrusions 101. Thus, the removable cap assembly 10 is prevented from moving into the first position, i.e. recapping.

The removable cap assembly 10 of the second embodiment of FIG. 8 can be seen in four sequential steps in FIG. 12. The aim of this figure is to depict the movement of the flaps 98a over the proximal portion and the receiving tab portion 78 of the removable cap assembly 10.

The first position (FIG. 12.a) shows the second outer protrusion 101 engaged with the opening 74, whereas the first outer protrusion 100 is positioned in the receiving tab portion 55 of the cap closer 5a. The tubular housing 2a is engaged to the outer tubular cap body 7a by the connection of the tab 78 to the tab 28. In FIG. 12.b illustrates the second outer protrusion 101 slightly disengaged from the opening 74, whereas the first outer protrusion 100 is partially free from the receiving tab portion 55 of the cap closer 5a. The outer tubular cap body 7a is barely disengaged from tubular housing 2a, thus a space is formed between the connection of the tab 78 and the tab 28. In FIG. 12.c is illustrated the second position when the second outer protrusion 101 is completely free from the opening 74. In FIG. 12.d is illustrated when the user tries to recap. The second outer protrusion 101 interacts with the opening 74 and hinders the outer tubular cap body 7a of moving back to the first position.

The inventive concept has mainly been described above with reference to the two detailed embodiments. However, as is readily appreciated by a person skilled in the art, other embodiments than the ones disclosed above are equally possible within the scope of the inventive concept, as defined by the appended claims.

The invention claimed is:

1. A medicament delivery device comprising:
   a housing having a proximal end and a distal end;
   a medicament container positioned in the housing;
   a medicament delivery mechanism associated with the medicament container;
   an activation member operably connected to the medicament delivery mechanism and longitudinally movable in relation to the housing from an extended position to a retracted position to activate the medicament delivery mechanism; and
   a removable cap assembly comprising an outer tubular cap body and an inner tubular integrity lock member coaxially coupled to the outer tubular cap body,
   wherein in a first position of the removable cap assembly, a resilient structure of the inner tubular integrity lock member is configured to interact with both a first engaging structure of the activation member and a second engaging structure of the housing for preventing the activation member from moving into the retracted position,
   wherein the first engaging structure of the activation member comprises a guiding recess and a guiding protrusion,
   wherein the guiding recess is U-shaped and it is defined by two parallel longitudinally extending side walls, a transversal side wall and a bottom wall and wherein the guiding protrusion is arranged on the outer surface of the bottom wall of the guiding recess,
   wherein the resilient structure of the inner tubular integrity lock member comprises a pair of spaced apart longitudinally extending arms which are flexible in the transversal direction and which define an opening between them, and
   wherein each longitudinally extending arm has a distal free end having a first transversal inwardly extending lip and a distal top edge.

2. The medicament delivery device according to claim 1, wherein in a second position of the removable cap assembly, the resilient structure of the inner tubular integrity lock member is configured to interact with the second engaging structure of the housing for preventing the removable cap assembly from moving into the first position.

3. The medicament delivery device according to claim 1, wherein the first transversal inwardly extending lip has a shape configured to interact with a corresponding shape of the guiding protrusion for allowing the longitudinally extending arm to flex.

4. The medicament delivery device according to claim 3, wherein in the first position of the removable cap assembly, the pair of spaced apart longitudinally extending arms are configured to extend longitudinally along the bottom wall of the U-shaped guiding recess and to receive the guiding protrusion in an opening defined by the pair of spaced apart longitudinally extending arms.

5. The medicament delivery device according to claim 4, wherein the second engaging structure is formed as a U shaped slot or cut-out defined by a transversal edge and two spaced apart and opposite side edges and wherein each side edge forms a transversal inwardly protrusion which presents an edge which forms part of a proximal rim of the housing.

6. The medicament delivery device according to claim 5, wherein each distal free end further comprises a second transversal outwardly extending lip which is releasably connected to a corresponding side edge of the U-shaped slot or cut-out of the housing for preventing the longitudinally extending arms to flex transversally outwards and thereby prevent the activation member from moving into the retracted position when the removable cap assembly is in the first position.

7. The medicament delivery device according to claim 6, wherein when the removable cap assembly is in the second position, the pair of spaced aparat longitudinally extending arms extended longitudinally along the bottom wall of the U-shaped guiding recess and each first transversal inwardly extending lip bears against the protrusion, and each distal top edge of the arms bears against the edge for preventing the removable cap assembly from moving into the first position.

8. The medicament delivery device according to claim 4, wherein the second engaging structure is the proximal rim of the housing.

9. The medicament delivery device according to claim 8, wherein in the first position of the removable cap assembly, the free ends of the extending arms are removably attached in a pocket defined by a portion of the first engaging structure and the second engaging structure, wherein the distal top edges bears against the transversal side wall and are placed at certain distance from the second engaging structure, and wherein the second engaging structure bears against the distal rim of the inner tubular integrity lock member.

10. The medicament delivery device according to claim 9, wherein the inner tubular integrity lock member comprises a flexible snap fit member or flap having a first outer end protrusion and a second outer protrusion along the flap which are configured to longitudinally interact with openings of a transversal wall of the outer tubular cap body.

11. The medicament delivery device according to claim 1, wherein the outer tubular cap body and the inner tubular integrity lock member are fixedly coupled or integrally manufactured.

12. The medicament delivery device according to claim 1, wherein the outer tubular cap body and the inner tubular integrity lock member are coupled longitudinally movable in relation to each other.

13. The medicament delivery device according to claim 1, wherein the medicament delivery device is an auto-injector.

14. A removable cap assembly for a medicament delivery device, the medicament delivery device including:
   a housing,
   a medicament container positioned in the housing,
   a medicament delivery mechanism associated with the medicament container, and
   an activation member operably connected to the medicament delivery mechanism and longitudinally movable in relation to the housing from an extended position to a retracted position to activate the medicament delivery mechanism,
   the removable cap assembly comprising:
   an outer tubular cap body and an inner tubular integrity lock member coaxially coupled to the outer tubular cap body,
   wherein in a first position of the removable cap assembly, a resilient structure of the inner tubular integrity lock member is configured to interact with both a first engaging structure of the activation member and a second engaging structure of the housing for preventing the activation member from moving into the retracted position, wherein in a second position of the removable cap assembly, the resilient structure of the inner tubular integrity lock member is configured to interact with the second engaging structure of the housing for preventing the removable cap assembly from moving into the first position.

15. The removable cap assembly according to claim 14, wherein the first engaging structure of the activation member comprises a guiding recess and a guiding protrusion.

* * * * *